United States Patent [19]

Day et al.

[11] Patent Number: 5,185,834
[45] Date of Patent: Feb. 9, 1993

[54] OPTICAL FIBER PROBES FOR REMOTE ANALYSIS

[75] Inventors: Leslie L. Day, Caterham; Graham Poulter, Orpington, both of England

[73] Assignee: Specac Ltd., Kent, England

[21] Appl. No.: 664,584

[22] Filed: Mar. 4, 1991

[51] Int. Cl.$^5$ .......................... G02B 6/00; G02B 6/36
[52] U.S. Cl. ........................................ 385/47; 385/45
[58] Field of Search ............... 350/96.10, 96.15, 96.18, 350/96.20, 96.29

[56] References Cited

U.S. PATENT DOCUMENTS

| | | | |
|---|---|---|---|
| 4,156,556 | 5/1979 | Klein et al. | 350/96.15 |
| 4,904,043 | 2/1990 | Schweizer | 350/96.15 X |
| 4,932,742 | 6/1990 | Tohme | 350/96.18 |
| 4,938,554 | 7/1990 | Wilson et al. | 350/96.15 |
| 4,938,555 | 7/1990 | Savage | 350/96.15 |
| 4,989,932 | 2/1991 | Landa et al. | 350/96.15 X |

*Primary Examiner*—Akm E. Ullah
*Attorney, Agent, or Firm*—Wallenstein, Wagner & Hattis, Ltd.

[57] ABSTRACT

An optical fibre probe for use with a spectrophotometer, for remote analysis of samples, includes a probe assembly having an outer tubular body member, a sleeve member, and a further tubular inner body member within that. Input and output optical fibres pass into the assembly from one end, and the fibres are terminated in ferrules secured within a ferrule plate which is mounted by means of grub screws at the end of the inner body member. Radiation emerging from the end face of the input optical fibre is reflected back within the probe to be focused on the end of the other fibre, after total internal reflection in the case of an ATR probe or after passing through a transparent sample in the case of a transmission probe. Lateral positioning of the ferrule plate and thus the ends of the optical fibres, across the optical axis, is achieved by differential tightening of the grub screws. Focusing is achieved by sliding the inner body member longitudinally in the sleeve member, and also rotating the inner body member if necessary. The inner body member and the sleeve member are then locked together by fully tightening the grub screws.

32 Claims, 13 Drawing Sheets

OPTICAL FIBER PROBES FOR REMOTE ANALYSIS

FIELD OF THE INVENTION

The present invention relates to optical fiber probes for remote analysis, and particularly for probes for use with spectrophotometers. Probes of this type permit the analysis of materials remote from the spectrophotometer, for example storage containers or in on-line process plant, thus removing the need to bring samples to the spectrophotometer and simplifying and speeding analysis. In particular, the present invention relates to the mechanical alignment, location and positioning system, by which the optical fibers are correctly related to the optical system of the probe.

DISCUSSION OF THE PRIOR ART

Remote optical sampling or testing using optical fiber probes is known per se. In the past, however, difficulties have been encountered in achieving proper alignment of the end surfaces of the optical fibers within the probe, and the present invention is intended at least to alleviate that difficulty.

SUMMARY OF THE INVENTION

It is an object of the present invention at least to alleviate the difficulties of the prior art.

The present invention provides a novel optical fiber probe, either of the transmission type or of the attenuated total reflection type, including improved means for positioning the ends of the optical fibers with respect to the optical axis of the probe and with respect to the optical system. In a preferred version of the invention, input and output optical fibers extend longitudinally within the probe, from one end, and terminate in plane ends within the probe. One of these ends acts as an emission source of radiation, the other to receive the radiation once it has past through the optical system of the probe. The ends are held at a fixed distance apart by means of a ferrule plate. The ferrule plate can be moved laterally (perpendicular to the optical axis) by means of four grub screws which are spaced around the periphery of the ferrule plate. The grub screws pass through a tubular inner body member and bear upon the ferrule plate inside that member. Thus, by differentially tightening opposing screws, the ferrule plate can be moved laterally across the optical axis.

The inner body member which carries the ferrule plate can be moved longitudinally of the probe. This enables the longitudinal position of the fibre ends to be adjusted, so ensuring that the radiation returning from the optical system can properly be focused on to the receiving end of the return or output fiber. In addition, the inner body member can be rotated about the axis to provide a further degree of freedom.

Preferably, the ends of the optical fibers lie in the same plane or at least are parallel to each other. The fibers themselves may extend parallel to each other along the length of the probe, so that the probe has a sampling end, for example for immersion in a liquid to be sampled, and a cable end having a cable through which the input and output optical fibres pass.

DESCRIPTION OF THE DRAWINGS

FIGS. 8(a)–(c) shows the ferrule plate of the probe of FIG. 1;

DESCRIPTION OF THE PREFERRED EMBODIMENTS

Figure 2:
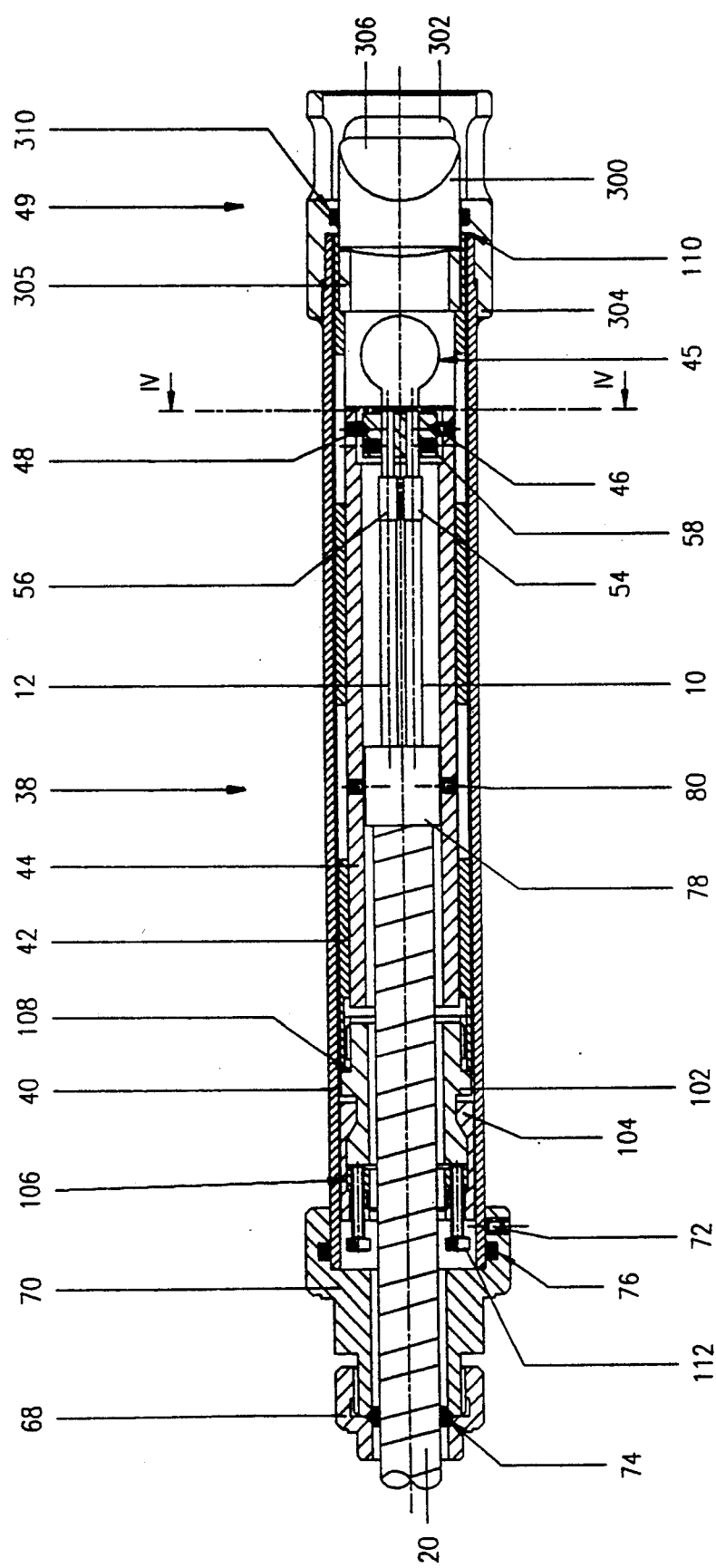
FIG. 2 is a longitudinal section through an optical fiber probe embodying the present invention.
Figure 3:
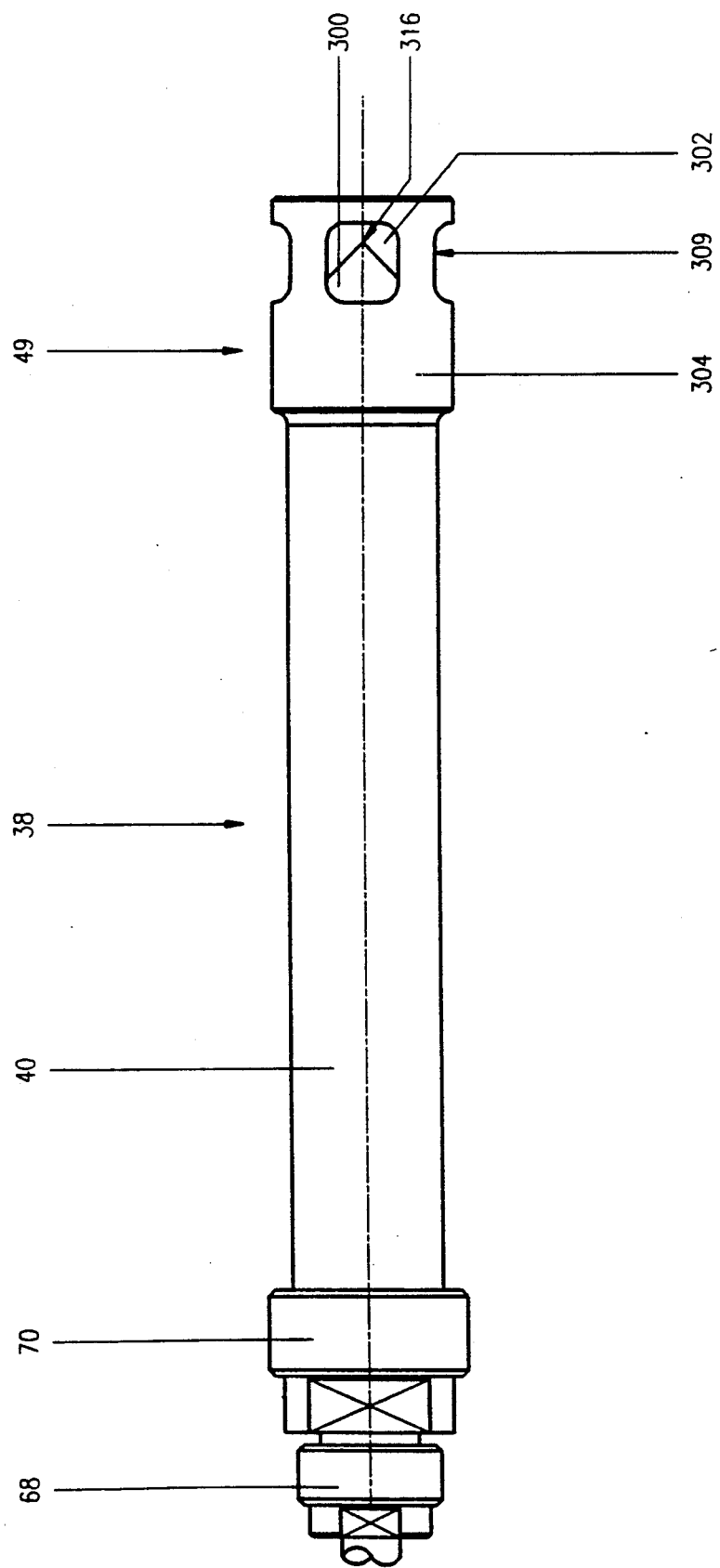
FIG. 3 is a side elevation of the probe of FIG. 2.
Figure 4:
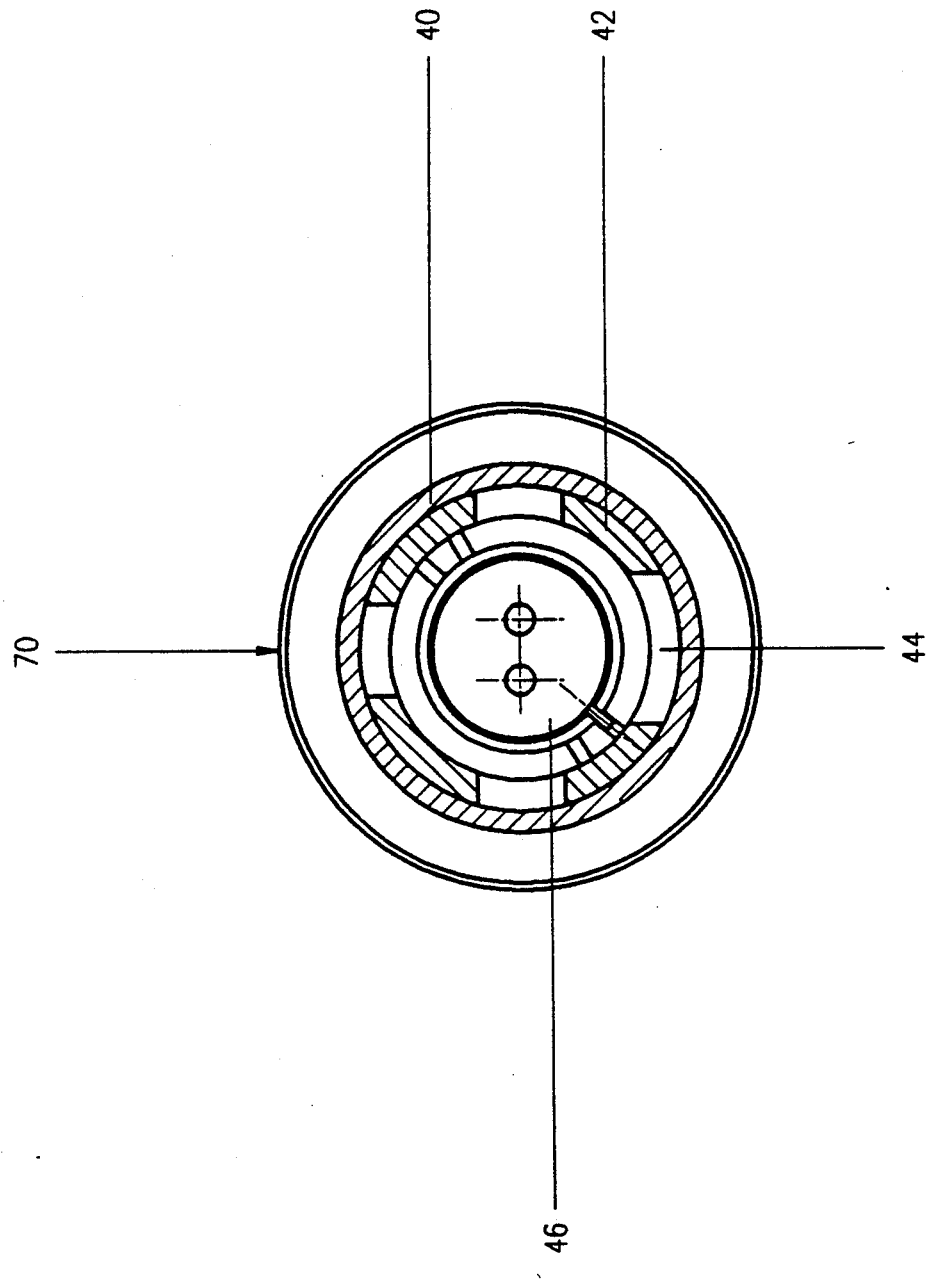
FIG. 4 is a section along the line IV–IV in FIG. 2.
Figure 10:
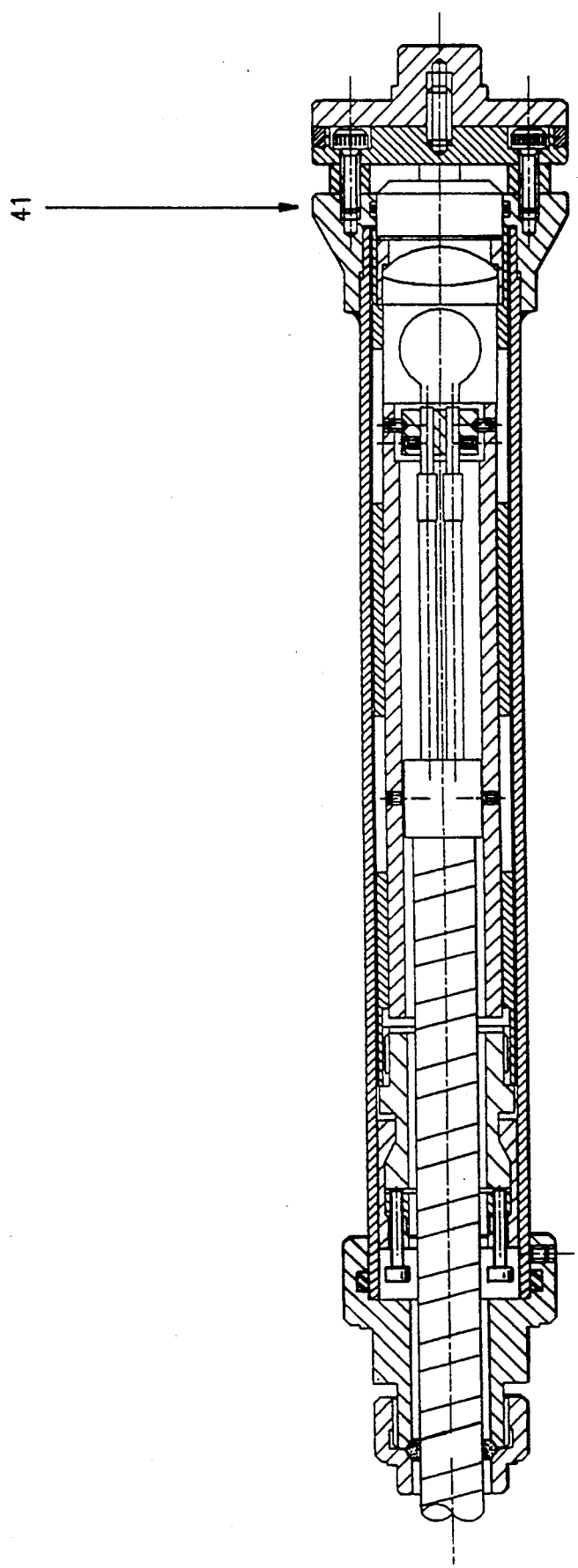
FIG. 10 is a longitudinal section through an alternative probe embodying the present invention.
Figure 11:
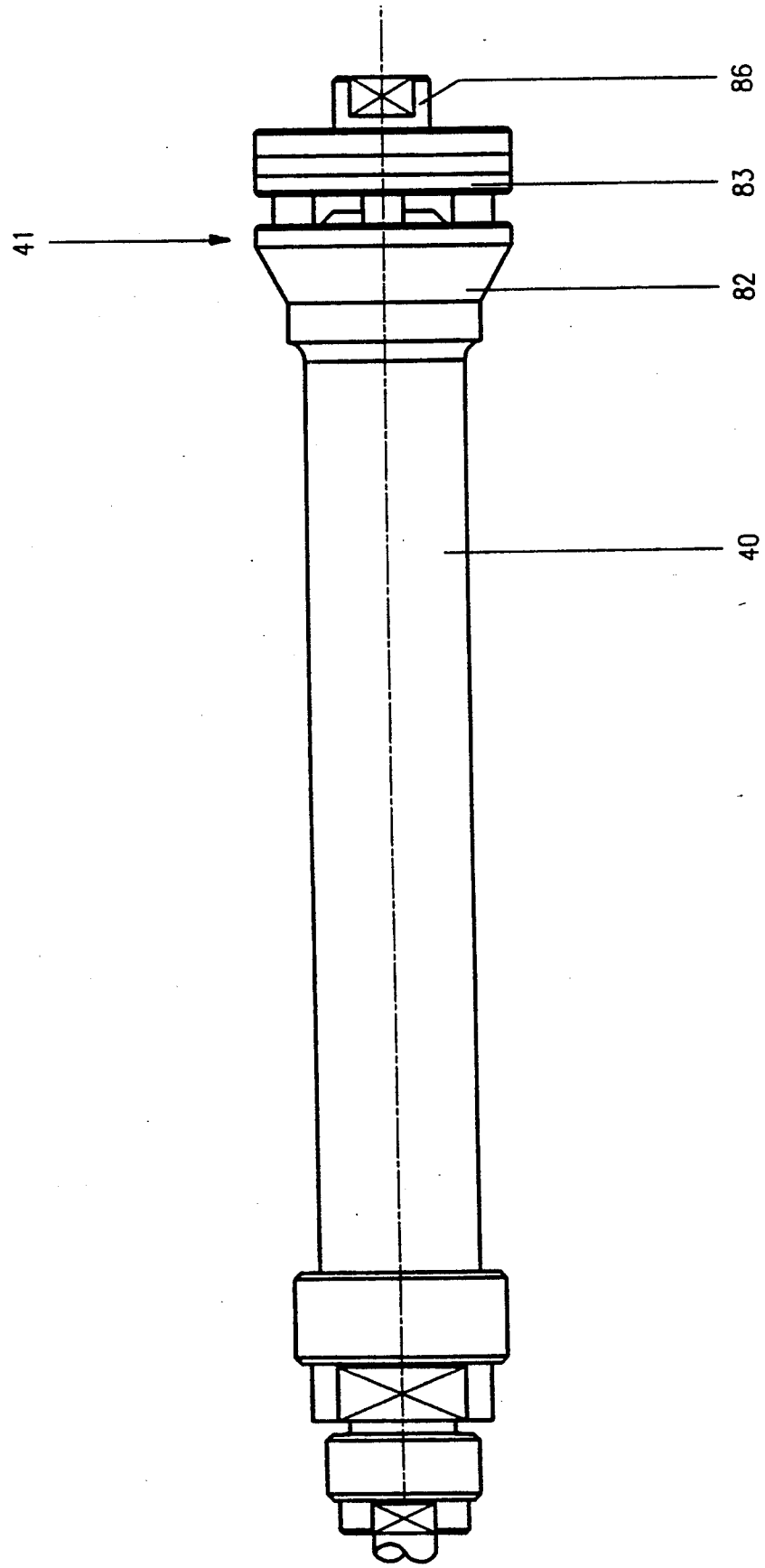
FIG. 11 is a side elevation of the probe of FIG. 10.

The first embodiment of the present invention is the optical fibre probe shown in detail in FIGS. 2–4. This is designed specifically for attenuated total reflectance (ATR) measurements on non-transmitting fluids and semi-solid samples, typically in the mid infra-red or near infra-red ranges (500 cm$^{-1}$ to 10000 cm$^{-1}$). The ranges stated must not, however, be considered as limiting, as the probe of the present invention may well be used, in appropriate circumstances, with wider ranges. The other embodiment, shown in detail in FIGS. 10 and 11, is specifically designed for optical transmission measurements in transparent sample fluids, typically in the near infra-red visible or ultra-violet ranges (5000 cm$^{-1}$ to 30000 cm$^{-1}$).

Both probes are of similar construction, and employ the same novel arrangements to enable optimum optical alignment between the optical fibers and the optical system of the probe to be readily achieved and subsequently maintained.

Figure 1:
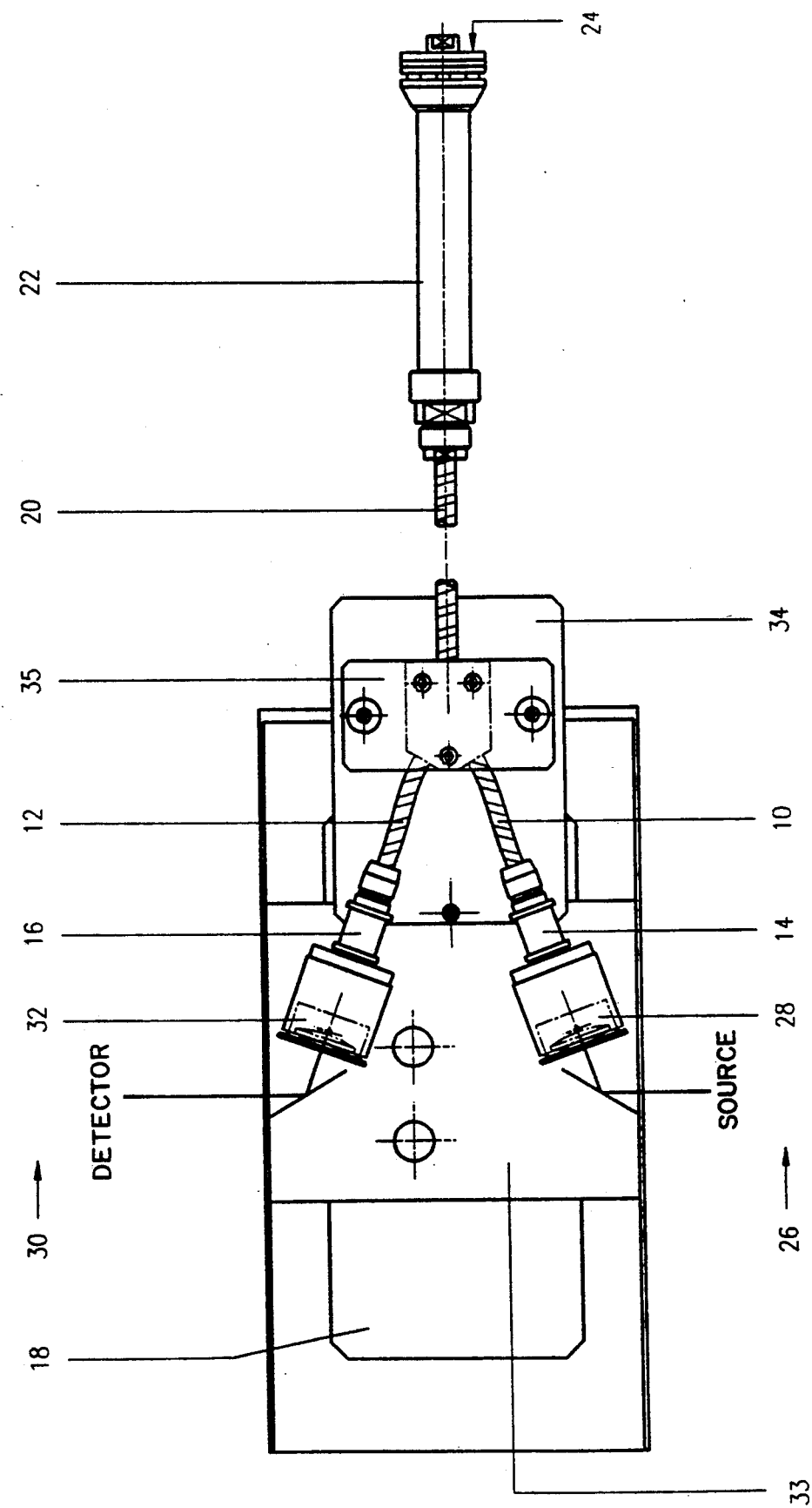
FIG. 1 illustrates diagrammatically the interconnection between an optical fiber probe embodying the present invention and an associated spectrophotometer.

FIG. 1 illustrates diagramatically the interconnection between either optical fiber probe and an associated spectrometer. In the figure, the transmission probe of FIGS. 10 and 11 is shown, but the ATR probe of FIGS. 2–4 is connected to a spectrometer in the same way.

The sample compartment 18 of a spectrophotometer (not shown) is adapted to receive mounting plates 33,34 to which are secured sheathed outward and return optical fibers 10,12 respectively terminating in connectors 14,16. The connectors are themselves secured to respective lens assemblies 28,32.

The individual optical fibers 10,12 are secured to the plate 34 by clamp 35, and both fibers then continue within a commonly sheathed cable 24 to the transmission probe assembly 22.

Radiation from the source optics 26 of the spectrophotometer passes into fiber 10 via lens assembly 28, is transmitted along the optical fiber 10 to the sampling head 24 of the probe 22, and then returns via the fiber 12 and the lens assembly 32 to the spectrophotometer detector optics 30.

Turning now to the attenuated total reflectance (ATR) probe assembly of FIGS. 2–4, it will be seen that the probe 38 itself has a tubular outer body 40 which contains as a sliding fit within it a tubular sleeve member 42. The sleeve member 42 in turn contains within it as a sliding fit a tubular inner body member 44. The sleeve member 42 is illustrated in more detail in FIG. 7 and the inner body member 44 is shown in more detail in FIG. 6.

The flexible optical fiber cable 20 which contains the optical fibres 10 and 12 enters the probe 38 through a cable clamping collar 68 which is screwed to an end cap 70. The end cap itself is a sliding fit on the outer end of the body 40 and is secured to it by means of a grub screw 72. Sealing between the cable 20 and the end cap 70 is provided by an o ring seal 74. Sealing between the end cap 70 and the body 40 is by means of another o ring seal 76.

The cable 20 continues down inside the inner body member 44 to a collar 78, where the sheathing terminates. The collar 78 is located and held in position in the inner body 44 by means of grub screws 80.

Figure 8B:
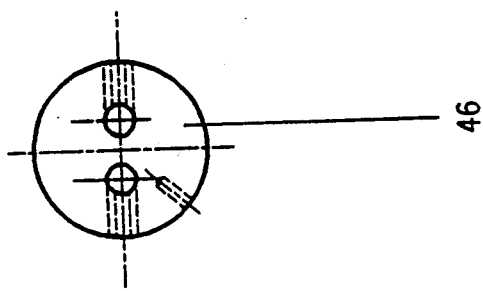
Figure 8A:
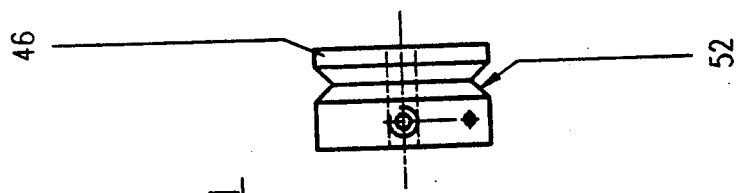

The individual sheathed optical cables 10,12 continue through the collar 78 to a ferrule plate 46 (FIG. 8) which is secured at the end of the inner body member 44 by grub screws 48. The ferrule plate 46 receives and holds in fixed lateral relationship to each other, ferrules 54,56 which terminate the optical fibers 10,12. The ferrules themselves pass through the ferrule plate 46 and are secured by grub screws 58 so as to hold the end faces of the optical fibres in a common plane proud of the end face of the ferrule plate 46. The ferrule plate and its respective grub screws 48 can be used to position the ends of the optical fibers as required, as will be explained in more detail later.

Figure 5:
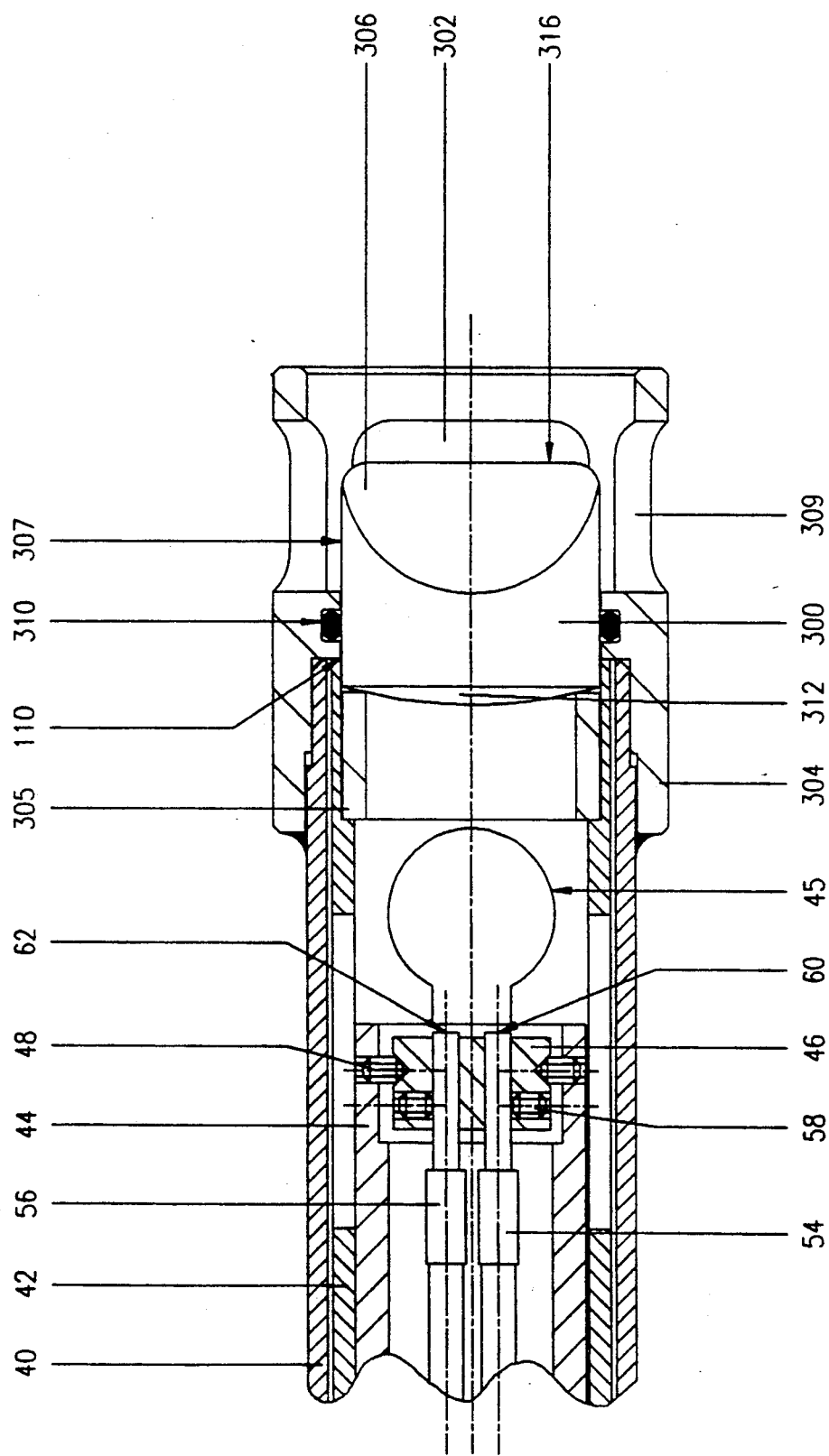
FIG. 5 is an enlarged longitudinal section of one end of the probe of FIG. 1.

The end of the ATR probe of FIG. 2 is shown in enlarged form in FIG. 5, and reference will now be made to that figure.

The far end of the sleeve member 42 is provided with a stepped bore within which is located an annular packing sleeve 305. Closing the end of the sleeve member 42, and located by the packing sleeve 305, is a one piece optical element 300 which provides focusing, collimation and reflection of the radiation beam incoming along the optical fibre 10. The optical element 300 is preferably made from zinc selenide, and has a shape that may be seen more clearly in FIGS. 9A and 9B. The peripheral edge 307 of the element is cylindrical. At one end there is a convex face 312, and at the other two perpendicular cut-away faces 306,308 which meet along a central ridge 316. The element essentially consists therefore of a cylindrical body having at one end a convex face and at the other end a roof prism. The element 300 is preferably 20 mm in diameter and has a total length of about 18 mm, but of course other sizes might be used depending upon the overall size of the ATR probe into which it is fitted. Materials other than zinc selenide, appropriate to the application and to the wavelength of the radiation in use, could also be used.

The element 300, mounted in the end of the sleeve member 42, protrudes into a sample compartment 302 formed in a protective end cap 304 which is welded or otherwise secured to the outer body member 40. The sample compartment has apertures 309 which permit the sample material to enter the compartment when the probe is in use, so coating the outer surfaces 306,308 of the element 300. Sealing between the element 300 and the wall of the end cap 304 is provided by an O ring seal 310; this prevents ingress of sample material into the interior of the probe.

Figure 9B:
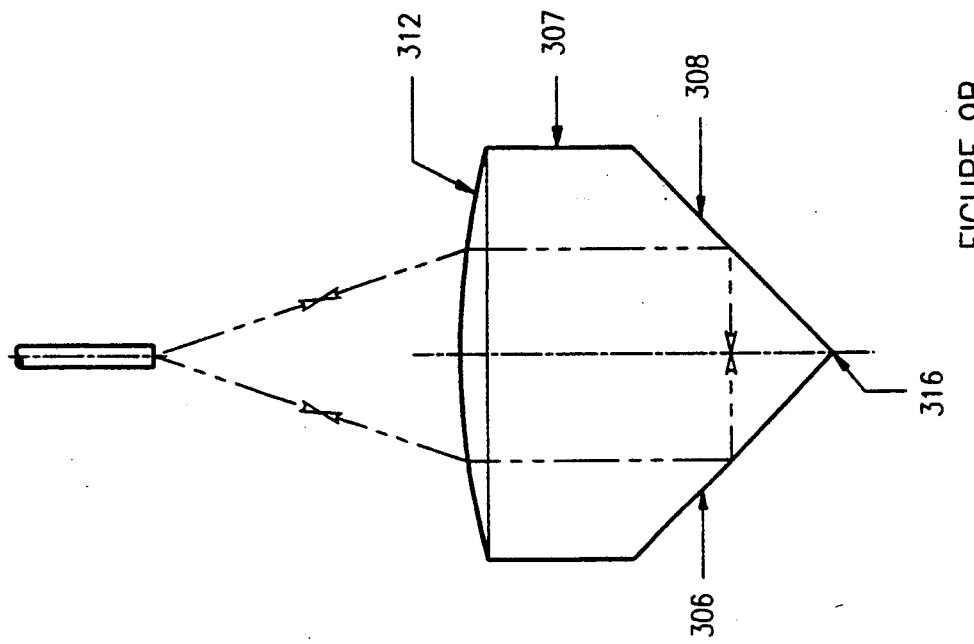
FIGS. 9A and 9B illustrate the optical system of the probe of FIG. 1.
Figure 9A:
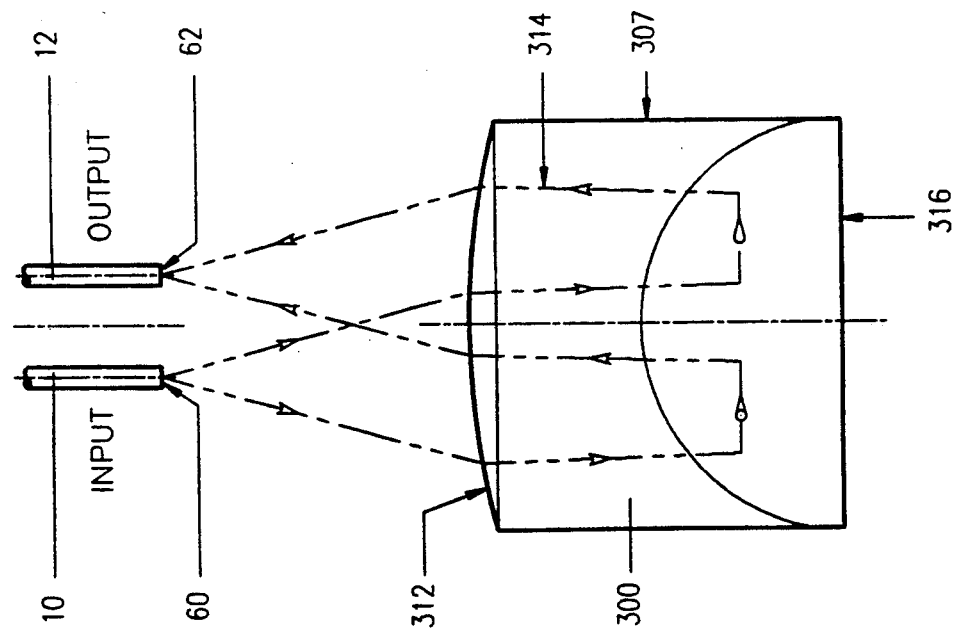

The operation of the probe is best demonstrated by a consideration of FIGS. 9A and 9B. Radiation from the spectrophotometer is sent along the optical fiber 10. Rays emerge from the end face 60 of that optical fiber, and are refracted by the convex face 312 of the element 300 to produce a parallel beam 314 which is incident upon the inner surfaces of the perpendicular faces 306, 308. The radiation is totally internally reflected at those faces and is directed back through the face 312 which focuses the beam upon the end face 62 of the output or return optical fiber 12. The radiation then passes along that fiber back to the spectrophotometer for analysis. When the beam is totally internally reflected on the faces 306,308, it picks up a spectrum which corresponds to the sample material which is at that time in contact with those two faces. Accordingly, the sample may be analysed by a consideration of the differences between the spectrum of the radiation sent out from the spectrophotometer, and that received back.

Employing a single composite reflecting and focusing element 300 eliminates the alignment problems which normally occur between separate elements of an ATR optical assembly. In addition, reflection losses are substantially reduced because of the lesser number of surfaces through which the radiation has to pass.

It will be appreciated that the exact alignment of the element 300 with respect to the ends 60,62, of the optical fibers is critical if the probe is to operate at optimal efficiency. In particular, the ridge 316 of the element 300 should lie in the same plane as the ends 60,62 of the optical fibers. In addition, the ends of the fibers must be so positioned that light emitted from the end 60 is accurately focused back on to the end 62 of the other fiber. The manner in which this is achieved will now be explained.

With the outer body member removed, rotational alignment may be achieved by rotating the inner body member 44, and with it the ferrule plate 46, with respect to the sleeve member 42 which carries the optical element 300. Focusing is achieved by sliding the inner body member longitudinally with respect to the sleeve member 42. While these adjustments are being done the output signal is being measured at the spectrophotometer, and when the correct position has been reached the grub screws 48 are tightened to lock the inner body member 44 in place within the sleeve member 42. As may best be seen in FIG. 7, the sleeve member 42 has longitudinal apertures through which the grub screws 48 may be reached from the outside. The purpose of the enlarged opening 45 (visible in FIGS. 2, 5 and 7) is to enable the person adjusting the device to see the ends 60, 62 of the optical fibers. This simply allows the adjustments to be carried out more easily.

Figure 6C:
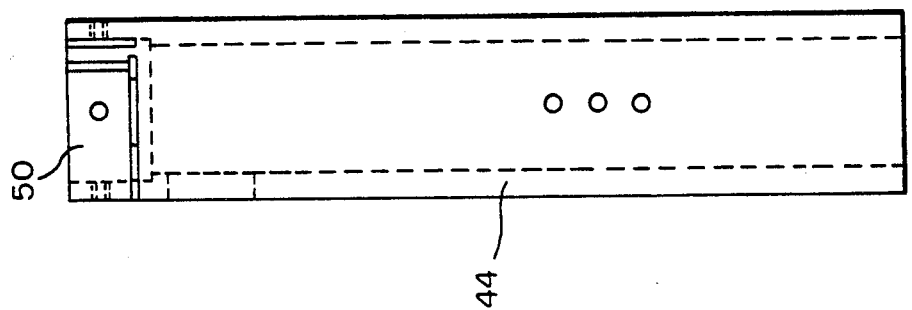
FIGS. 6(a)–(c) shows the inner body member of the probe of FIG. 1.
Figure 6B:
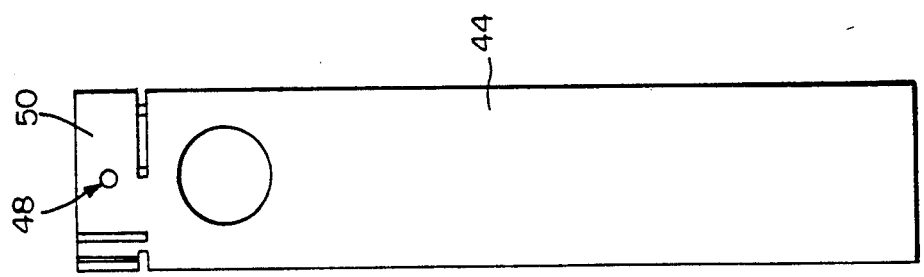
Figure 6A:
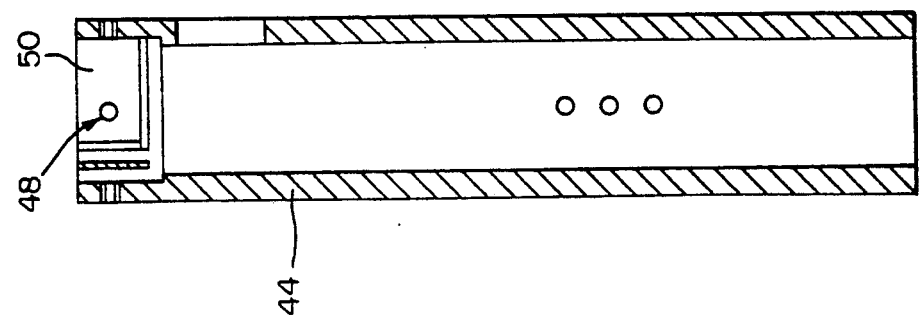
Figure 7A:
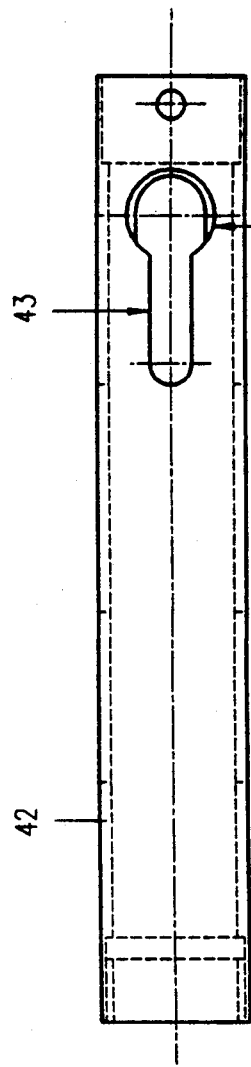
FIGS. 7(a)–(c) shows the sleeve member of the probe of FIG. 1.
Figure 7B:
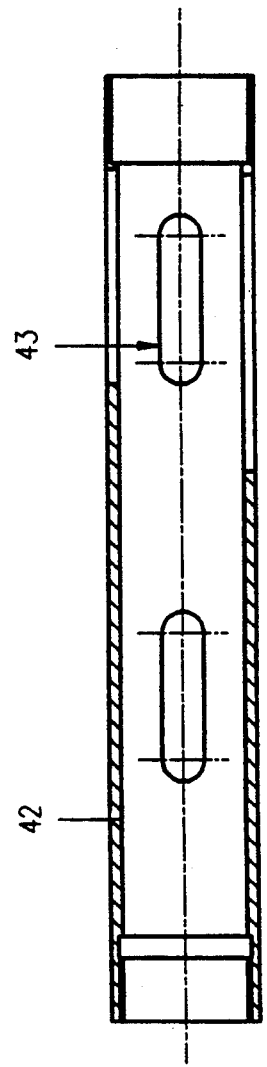
Figure 7C:
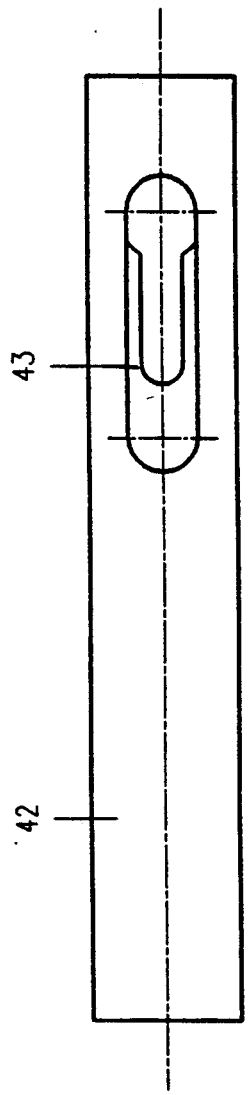

As may be seen in FIG. 6, the grub screws 48 engage in tapped apertures in circumferential tongues 50 formed at the end of the inner body member. The inner ends of these grub screws locate in a circumferential groove 52 of the ferrule plate 46, as may be seen in FIG. 8. Thus, in addition to securing the ferrule plate 46 within the inner body member 44, the grub screws 48 if further tightened deflect the circumferential grooves 50 outwardly to engage the adjacent inner surface of the sleeve member 42, so locking the inner body member and the sleeve member 42 together.

To achieve optimal performance, it may be desired to move the ferrule plate 46 laterally, that is in either of the two directions perpendicular to the axis of the probe. The grub screws 48 may be used for this purpose. Four grub screws are provided, equally spaced around the periphery of the inner body member 44, and if one of these screws is tightened at the same time as the opposite screw is loosened, the ferrule plate will move laterally towards the tightening screw. The plate can of course be moved in the perpendicular lateral direction by tightening and loosening the other pair of grub screws. When the plate is correctly positioned, each pair of opposing grub screws is tightened fully, using two allen keys at once so that one screw is tightened against the other. In this way, the screws can be tightened to secure the inner body member 44 to the sleeve member 42 without altering the lateral position of the ferrule plate 46.

Once focusing and alignment have been achieved, and the grub screws 48 fully tightened to lock the inner body member to the sleeve member, the outer body member 40 is then pushed over the partially completed assembly, with the O ring 310 moving down over the cylindrical surface 307 of the optical element 300. The outer body member 40 can then be secured in position. This is achieved by the combination of insert ring 102, split packing ring 104 and screw ring 106 (see FIG. 2). The insert 102 screws into the upper end of the inner body member 44 and has a shoulder 108 which engages the left hand end of the sleeve 42. In turn, the lower end of the sleeve member 42 engages upon a shoulder 110 at the lower end of the inner body member 44. The split packing ring 104 surrounds the upper part of the insert 102 and has clearance holes in its upper face through which screws 112, mounted in tapped holes in the screw ring 106, pass.

When the screws 112 are tightened upon the insert 102, the lower part of the split packing ring 104 is forced outwardly towards the edges of the wall of the outer body member 40 by means of a wedging action between the insert 102 and the packing ring 104.

This locks the inner body and sleeve assembly to the outer body 40, so enabling the ATR probe 38 to resist longitudinal forces which might be applied in use, for example if the probe is assembled into an aperture in the wall of a pipe line or pressure chamber.

To complete the ATR probe, the end cap 70 is pushed down over the end of the outer body member 40 and secured in position by the grub screws 72.

Figure 12:
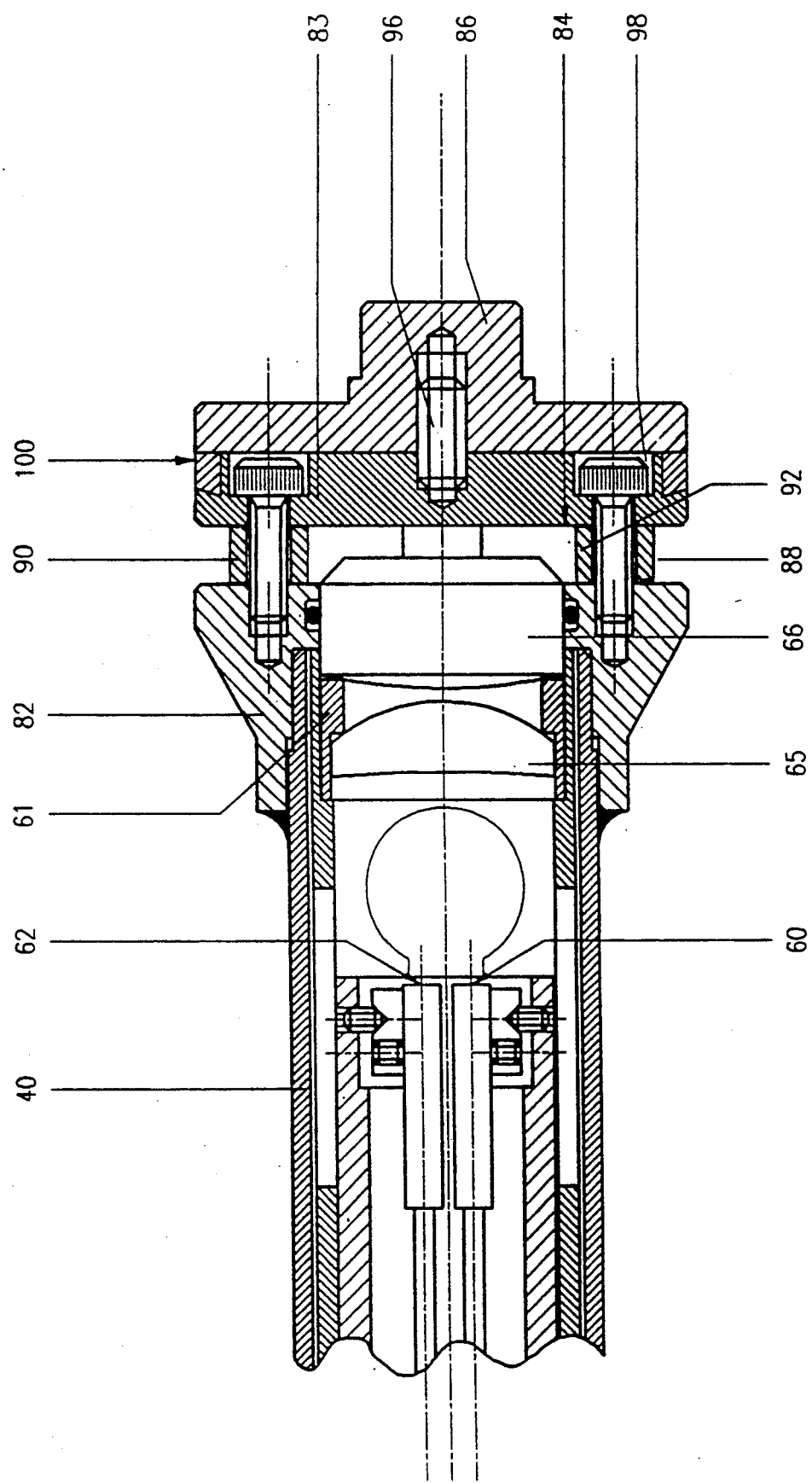
FIG. 12 is an enlarged partial longitudinal section showing one end of the probe of FIG. 10.

A second embodiment of the invention is shown in FIGS. 10-12, this being a probe designed for optical transmission measurements on transparent sample fluids. The sampling head of the probe 41 differs from that of the ATR probe already described, but all other details are identical.

The end of the outer body member 40 in this embodiment carries a mounting flange 82 to which is secured the elements of the sampling head, including a stainless steel member 83 having a mirror surface 84 and a cover member 86. The member 83 is mounted upon the flange 82 by means of screws 88 and is separated from a lens assembly 66 by spacers 90. This leaves a space 92 between the exterior face of the lens assembly 66 and the mirror surface 84 into which sample liquid may flow. The length of the spacers 90 is chosen to provide the desired optical path length between the lens assembly 66 and the mirror surface 84.

The cover 86 is secured to the rear of the member 83 by a stud 96, thereby covering the apertures 98 containing the screws 88. Sealing between the cover 86 and the apertures 98 is provided by a PTFE machined square section ring seal 100 to prevent contamination of the apertures and screw heads by the sample liquid. In the embodiment shown, there is an additional optical element 65, which is spaced from the primary optical element 66 by a spacer sleeve 61. Depending upon the application, this element may be omitted or combined with the main optical element 66.

Figure 13:
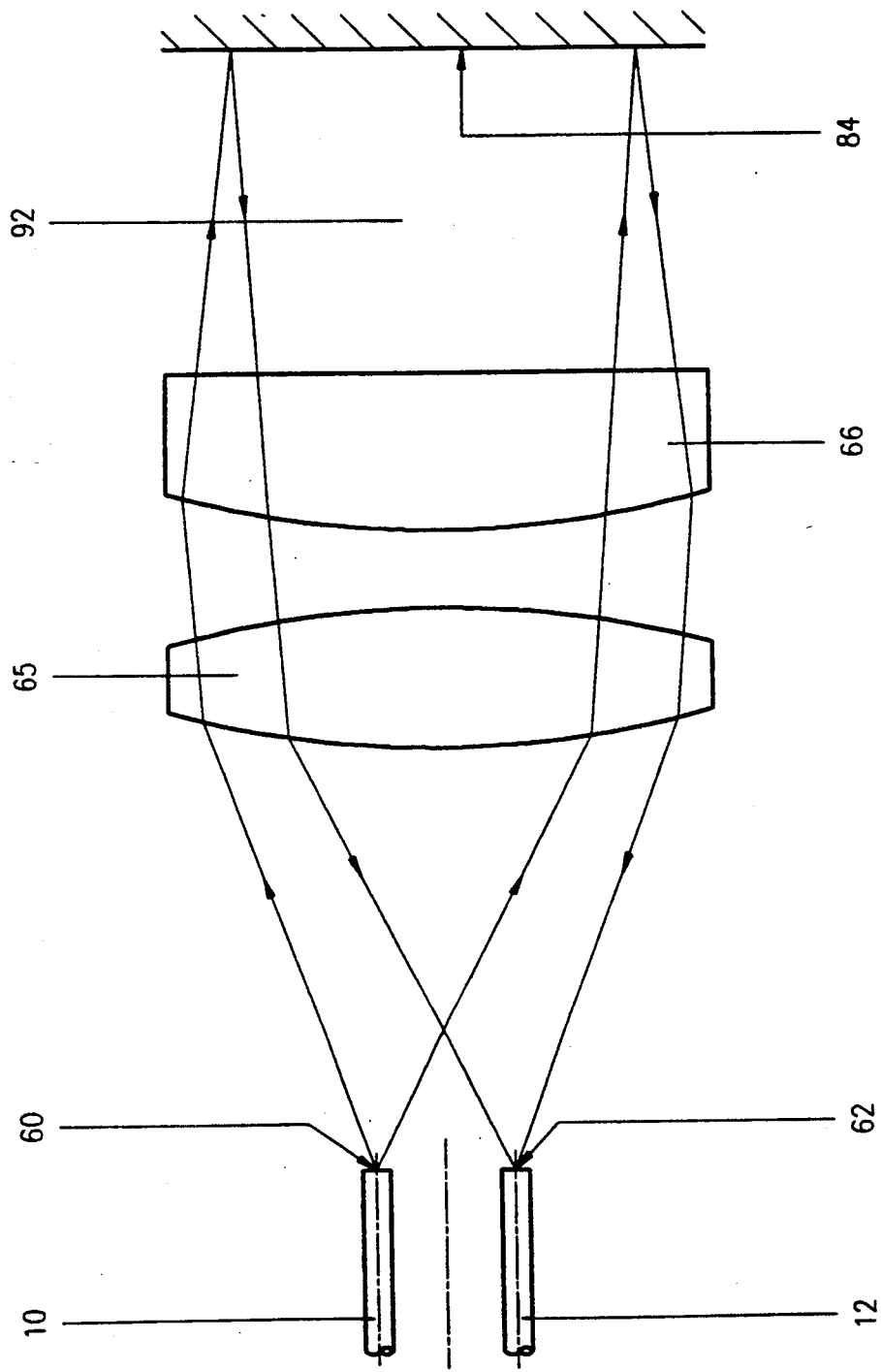
FIG. 13 illustrates the optical arrangement of the probe of FIG. 10.

The optical system of this embodiment is illustrated schematically in FIG. 13. An input beam emerging from the end face 60 of the fiber 10 is collimated by the lens assemblies 65, 66, and after traversing the sample space 92 is reflected by the mirror surface 84, back through the lens assemblies 66, 65 to be re-focused on the end face 62 of the other optical fiber 12.

Optimal alignment of the end faces 60, 62 of the optical fibers 10, 12 is achieved in the same way as with the other embodiment, that is by translating the ferrule plate 46 across the optical axis of the optical assembly. Focusing is achieved by longitudinal movement of the inner body member 44 relative to the sleeve member 42 which mounts the lens assemblies 65, 66. Finally, the inner body 44 is secured in the desired position within the sleeve 42 once optimal alignment and focusing have been achieved.

What is claimed is:

1. An optical fiber probe for remote testing of a sample, said probe including:
   a tubular sleeve member;
   an input optical fiber extending within and longitudinally of said sleeve member and having an end so aligned that radiation is emitted generally along said axis in a given longitudinal direction;
   an output optical fiber extending within and longitudinally of said sleeve member and having an end aligned for collection of radiation propagating generally along said axis in a direction opposite to said given longitudinal direction;
   a back reflecting sampling head disposed on said axis having means for receiving radiation emitted from said end of said input optical fiber, means for bringing said radiation into contact with said sample to be tested and means for subsequently focusing said radiation onto said end of said output optical fiber; and
   adjustable mounting means for mounting said optical fibers within said sleeve member so that the position of said ends with respect to said sampling head may be adjusted.

2. An optical fiber probe according to claim 1 wherein the adjustable mounting means includes an inner tubular body member mounted for sliding adjustment within said sleeve member.

3. An optical fiber probe as defined in claim 2 wherein said inner body member is also mounted for rotational adjustment within said sleeve member.

4. An optical fiber probe as defined in claim 2 wherein said adjustable mounting means includes a mounting block mounted within said inner body member and arranged to hold said ends of said optical fibers at spaced locations.

5. An optical fiber probe as defined in claim 4 wherein said mounting block comprises a ferrule plate, said ferrule plate having ferrules for receiving and locating said ends of said optical fibers.

6. An optical fiber probe as defined in claim 5 wherein said ferrules hold said optical fibers so that said ends of said optical fibers are protuberant of said ferrule plate.

7. An optical fiber probe as defined in claim 4 wherein said sleeve member has an axis, said mounting block being mounted for lateral adjustment in at least one direction perpendicular to said axis of said sleeve member.

8. An optical fiber probe as defined in claim 7 wherein said mounting block is mounted for lateral adjustment in two perpendicular directions, each perpendicular to said axis of said sleeve member.

9. An optical fiber probe as defined in claim 7 wherein said mounting block is secured to said inner body member by screw means, said lateral adjustment being effected by differential tightening of said screw means.

10. An optical fiber probe as defined in claim 9 wherein said screw means are arranged in addition to lock said inner body member in position with respect to said sleeve member.

11. An optical fiber probe as defined in claim 10 wherein said inner body member is locked in position with respect to said sleeve member by tightening said screw means one against another.

12. An optical fiber probe as defined in claim 10 wherein said inner body member includes tongues-which, when said screw means are tightened, deform outwardly to lock said inner body member in position with respect to said sleeve member.

13. An optical fiber probe as defined in claim 9 wherein said sleeve member defines apertures therein, said apertures giving access to said screw means.

14. An optical fiber probe as defined in claim 13 wherein said sleeve member further defines an opening therein, said opening giving a sight through said sleeve member to said ends of said optical fibers.

15. An optical fiber probe as defined in claim 1 wherein said adjustable mounting means includes a mounting block arranged to hold said ends of said optical fibers at spaced locations.

16. An optical fiber probe as defined in claim 15 wherein said mounting block comprises a ferrule plate, said ferrule plate having ferrules for receiving and locating said ends of said optical fibers.

17. An optical fiber probe as defined in claim 16 wherein said ferrules hold said optical fibers so that said ends of said optical fibers are protuberant of said ferrule plate.

18. An optical fiber probe as defined in claim 15 wherein said sleeve member has an axis, said mounting block being mounted for lateral adjustment, in at least one direction perpendicular to said axis of said sleeve member.

19. An optical fiber probe as defined in claim 18 wherein said mounting block is mounted for lateral adjustment in two perpendicular directions, each perpendicular to said axis of said sleeve member.

20. An optical fiber probe as defined in claim 18 including screw means for effecting said lateral adjustment.

21. An optical fiber probe as defined in claim 20 wherein said screw means are arranged in addition to lock said mounting block in a fixed position with respect to said sleeve member.

22. An optical fiber probe as defined in claim 20 wherein said sleeve member further defines an opening therein, said opening giving a sight through said sleeve member to said ends of said optical fibers.

23. An optical fiber probe as defined in claim 7 including screw means for effecting said lateral adjustment.

24. An optical fiber probe as defined in claim 23 wherein said screw means are arranged in addition to lock said inner body member in a fixed position with respect to said sleeve member.

25. An optical fiber probe as defined in claim 23 wherein said screw means extend through said inner body member and bear upon said mounting block within said inner body member.

26. An optical fiber probe as defined in claim 1 wherein said ends of said optical fibers are substantially parallel to one another.

27. A optical fiber probe as defined in claim 26 wherein said ends of said optical fibers lie substantially in a common plane.

28. An optical fiber probe as defined in claim 1 including an outer tubular body member surrounding said sleeve member.

29. An optical fiber probe as defined in claim 28 including means for locking said sleeve member with respect to said outer tubular body member.

30. An optical fiber probe as defined in claim 1 wherein said probe is a transmission probe, said sampling head having means for receiving a sample and means for directing said radiation through said sample.

31. An optical fiber probe as defined in claim 1 wherein said probe is an attenuated total reflectance probe, said sampling head having a total internal reflection element providing back reflection, said element having at least one surface for total internal reflection, means for directing said radiation into said element for reflection from said surface, and means for receiving a sample in contact with said surface.

32. An optical fiber probe for remote testing of a sample, said probe including:
  a tubular sleeve member;
  an input optical fiber extending within and longitudinally of said sleeve member and having an end so aligned that radiation is emitted generally along said axis in a given longitudinal direction;
  an output optical fiber extending within and longitudinally of said sleeve member and having an end aligned for collection of radiation propagating generally along said axis in a direction opposite to said given longitudinal direction;
  a back reflecting sampling head disposed on said axis having means for receiving radiation emitted from said end of said input optical fiber, means for bringing said radiation into contact with said sample to be tested and means for subsequently focusing said radiation onto said end of said output optical fiber;
  anda tubular inner body member mounted within said sleeve member for longitudinal and rotational adjustment within said sleeve member, said inner body member having an axis; and
  a mounting block for mounting said optical fibers to hold said ends of said optical fibers spaced apart from one another, said mounting block being adjustably mounted within said inner body member for adjustment in at least one direction perpendicular to said axis.

* * * * *